United States Patent [19]
Thomsen et al.

[11] Patent Number: 6,011,006
[45] Date of Patent: Jan. 4, 2000

[54] METHOD OF TREATING HOT FLUSHES WITH HEXAPEPTIDES

[75] Inventors: Christian Thomsen, Strøby; Joel Martin, Gentofte; Nils Langeland Johansen; Philip Just Larsen, both of København; Rolf Hohlweg, Kvistgaard, all of Denmark

[73] Assignee: Novo Nordisk A/S, Bagsvaerd, Denmark

[21] Appl. No.: 09/261,367

[22] Filed: Mar. 3, 1999

Related U.S. Application Data

[60] Provisional application No. 60/079,548, Mar. 27, 1998.

[30] Foreign Application Priority Data

Mar. 5, 1998 [DK] Denmark ................. 0297/98

[51] Int. Cl.$^7$ ........................................... A61K 38/00
[52] U.S. Cl. ........................................................ 514/2
[58] Field of Search ......................................... 514/2

[56] References Cited

U.S. PATENT DOCUMENTS

| | | | |
|---|---|---|---|
| 4,663,435 | 5/1987 | Brady | 530/311 |
| 5,386,011 | 1/1995 | Wiedeman et al. | 530/329 |

*Primary Examiner*—Raymond Henley, III
*Attorney, Agent, or Firm*—Steve T. Zelson; Carol E. Rozek

[57] ABSTRACT

The present invention relates to a method of treating migraine, non-insulin dependent diabetes mellitus (type II diabetes), sepsis, inflammation and/or vasomotor disturbances. This method utilizes a hexapeptide of formula (I)

$$A^1\text{-}A^2\text{-}A^3\text{-}A^4\text{-}A^5\text{-}A^6\text{-}Y \qquad (I)$$

wherein $A^1$, $A^2$, $A^3$, $A^4$, $A^5$, $A^6$ and Y are as defined in the specification.

14 Claims, No Drawings

METHOD OF TREATING HOT FLUSHES WITH HEXAPEPTIDES

CROSS-REFERENCE TO RELATED APPLICATIONS

This application claims priority under 35 U.S.C. 119 of U.S. provisional application No. 60/079,548 filed Mar. 27, 1998 and Danish application no. 0297/98 filed Mar. 5, 1998, the contents of which are fully incorporated herein by reference.

FIELD OF INVENTION

The present invention relates to the use of compounds of formula I for the treatment of migraine, non-insulin dependent diabetes mellitus (type II diabetes), sepsis, inflammation and/or vasomotor disturbances, in particular the peripheral vasomotor effects known as hot flushes or hot flashes. The present invention also embraces pharmaceutical compositions comprising these compounds and methods of using the compounds and their pharmaceutical compositions.

BACKGROUND OF THE INVENTION

A "hot flush" is a sudden transient sensation ranging from warmth to intense heat and typically accompanied by flushing and perspiration. It is the classic sign of the menopause and the predominant complaint of menopausal women. Epidemiological studies report that the majority of menopausal women experience hot flushes, although with large variation in frequency and intensity (Treatment of the Postmenopausal Woman, Basic and Clinical Aspects, Raven Press 1994, ed. R. A. Lobo).

A positive correlation between plasma levels of calcitonin gene-related peptide (CGRP) and frequency of hot flushes in women has recently been reported (Chen et al., 1993, Lancet (342) 49), in accordance with the potent vasodilatory effect of CGRP (Brain et al., 1985, Nature, (313) 54–56).

Also, a positive correlation between CGRP antagonists and diabetes, septic shock and inflammation has been described (Feurstein, G, Willette, R and Aiyar, N., 1995, Can. J. Physiol. Pharmacol. 73: 1070–1074).

Recently, a novel heptadeca peptide, nociceptin, was discovered (Meunier et al., 1995, Nature (377) 532–535, Reinscheid et al., 1995, Science (270) 792–794).

Nociceptin and analogues thereof have been disclosed in WO 97/07212, EP 813065 and in WO 97/07208. These peptides and inhibitors thereof are said to be useful for antagonizing physiologic effects of an opioid in an animal, and for treating/preventing a disease related to: hyperalgesia, neuroendocrine secretion, stress, locomotor activity, anxiety etc.

Jenck, F et. al. also found, that Orphanin FQ acts as an anxiolytic to attenuate behavioral-responses to stress (PNAS Vol. 94, 1997).

Recently, Dooley, C,T et. al. found hexapeptides having the same affinity for the opioid-like receptor ORL1 as nociceptin with binding in the nanomolar range (Binding and In Vitro Activities of Peptides with High Affinity for Nociceptin/Orphanin FQ Receptor, ORL1. Journal of Pharmacology and Experimental Therapeutics, (1997) Vol. 283, No.2: 735–741).

SUMMARY OF THE INVENTION

The present invention provides for the use of a compound selected from a basic hexapeptide or a pharmaceutically acceptable salt thereof, for the preparation of a pharmaceutical composition for the treatment of Type II diabetes, septic shock, inflammation and vasomotor disturbances, in particular the peripheral vasomotor effects known as hot flushes or hot flashes.

Further objects will become apparent from the following description.

DETAILED DESCRIPTION OF THE INVENTION

It has been found recently that hexapeptides with L or D basic amino acids in position $A^1$, $A^4$ and/or $A^6$, aromatic L or D amino acids in position $A^2$ and/or $A^3$ and/or aromatic or aliphatic L or D amino acids in position $A^5$ have the same affinity for the opioid-like receptor ORL1 as nociceptin with binding in the nanomolar range (Dooley, C,T et. al., Binding and In Vitro Activities of Peptides with High Affinity for Nociceptin/Orphanin FQ Receptor, ORL1. Journal of Pharmacology and Experimental Therapeutics, (1997) Vol. 283, No.2: 735–741).

Accordingly, in a first aspect, the present invention relates to the use of a compound of the general formula I $$A^1\text{-}A^2\text{-}A^3\text{-}A^4\text{-}A^5\text{-}A^6\text{-}Y \qquad (I)$$

wherein $A^1$ is Arg, Lys, His, D-Arg, D-Lys, D-His, acylated Arg, acylated Lys, acylated His, acylated D-Arg, acylated D-Lys or acylated D-His;

$A^2$ is Tyr, Trp, Phe, D-Tyr, D-Trp or D-Phe;

$A^3$ is Tyr, Trp, Phe, D-Tyr, D-Trp or D-Phe;

$A^4$ is Lys, Arg, His, D-Arg, D-Lys or D-His;

$A^5$ is Phe, Tyr, Trp, Ile, D-Phe, D-Tyr, D-Trp or D-Ile;

$A^6$ is Arg, Lys, His, D-Arg, D-Lys or D-His and

Y is OH or $NH_2$ or a pharmaceutically acceptable salt thereof, for the preparation of a pharmaceutical composition for the treatment of Type II diabetes, septic shock, inflammation and vasomotor disturbances, in particular the peripheral vasomotor effects known as hot flushes or hot flashes.

In one embodiment of the invention the compound of the formula I is selected from the group consisting of Ac-Arg-Tyr-Tyr-Arg-Trp-Arg-$NH_2$, Ac-Arg-Tyr-Tyr-Arg-Trp-Lys-$NH_2$, Ac-Arg-Tyr-Tyr-Arg-Ile-Lys-$NH_2$, Ac-Arg-Tyr-Tyr-Lys-Trp-Arg-$NH_2$ and Ac-Arg-Tyr-Tyr-Lys-Trp-Lys-$NH_2$.

(all of which, e.g., are produced using commonly known solid phase peptide synthesis technology).

The term Ac is intended to mean acetylated.

In another embodiment of the invention the composition is in a form suitable for oral, nasal, transdermal, pulmonal, or parenteral administration.

In a further embodiment of the first aspect the compound of the formula I is administered as a dose in the range from about 0.001 to about 10 g per patient per day, preferably from about 1 to about 1000 mg per patient per day, especially from about 10 to about 100 mg per patient per day, e.g. about 100 mg per patient per day.

In still another embodiment of the first aspect the amino acids are all in either the D or L stereochemical configuration, preferably the L stereochemical configuration. However, the compounds of the invention may comprise both L and D amino acids.

In a second aspect the invention relates to a method for the treatment or prevention of migraine, Type II diabetes, sepsis, inflammation and/or vasomotor disturbances, in particular the peripheral vasomotor effects known as hot flushes or hot flashes, the method comprising administering to a patient in need thereof an effective amount of compound of the formula I or a pharmaceutically acceptable salt thereof.

The therapeutically effective amount of a compound of the formula I will depend upon the mode of administration, on the therapy desired, the form in which administered, the subject to be treated, the body weight of the subject to be treated, and the preference and experience of the physician or veterinarian in charge.

In one embodiment of the second aspect the compound of the formula I is administered as a dose with an effective amount in the range from about 0.001 to about 10 g per patient per day, preferably from about 1 to about 1000 mg per patient per day, especially from about 10 to about 100 mg per patient per day, e.g. about 100 mg per patient per day.

Within its scope the invention includes the D and/or L stereochemical configuration of all the amino acids which constitute the compound of the formula I.

As used herein the term "patient" comprises any mammal which may benefit from treatment or prevention of vasomotor disturbances, such as a human, especially if the mammal is a female, such as a woman. However, "patient" is not intended to be limited to a woman.

The compounds intended to be embraced by the present invention are such peptides which are disclosed in Journal of Pharmacology and Experimental Therapeutics, (1997) Vol. 283, No.2: 735–741.

As used herein the term "treatment" is also meant to comprise prophylactic treatment.

Within the present invention, the compound of the formula I may be prepared in the form of pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulphuric and phosphoric acids and the like. Further examples of pharmaceutically acceptable inorganic or organic acid addition salts include the pharmaceutically acceptable salts listed in *Journal of Pharmaceutical Science*, 66, 2 (1977) which are known to the skilled artisan.

Also intended as pharmaceutically acceptable acid addition salts are the hydrates which the present compounds of the formula I are able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of the formula I of this invention may form solvates with standard low molecular weight solvents using methods known to a person skilled in the art.

The compound of the formula I may be administered in pharmaceutically acceptable acid addition salt form. Such salt forms are believed to exhibit approximately the same order of activity as the free base forms.

A pharmaceutical composition for use in accordance with the present invention comprises one or more compounds of the formula I as active ingredient(s), or a pharmaceutically acceptable salt thereof, together with a pharmaceutically acceptable carrier or diluent.

Pharmaceutical compositions containing compounds of the formula I of the present invention may be prepared by conventional techniques, e.g., as described in *Remington: The Science and Practise of Pharmacy*, 19$^{th}$ Ed., 1995. The compositions may appear in conventional forms, for example capsules, tablets, aerosols, solutions, suspensions or topical applications.

Typical compositions include hexapeptides or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of an ampule, capsule, sachet, paper, or other container. When the carrier serves as a diluent, it may be solid, semi-solid, or liquid material which acts as a vehicle, excipient, or medium for the active compound. The active compound can be adsorbed on a granular solid container, for example in a sachet. Some examples of suitable carriers are water, salt solutions, alcohols, polyethylene glycols, polyhydroxyethoxylated castor oil, peanut oil, olive oil, gelatin, lactose, terra alba, sucrose, cyclodextrin, amylose, magnesium stearate, talc, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or coloring substances and the like, which do not deleteriously react with the active compounds.

The route of administration may be any route which effectively transports the active compound to the appropriate or desired site of action, such as oral, nasal, pulmonary, transdermal or parenteral, e.g., rectal, depot, subcutaneous, intravenous, intraurethral, intramuscular, intranasal, ophthalmic solution or an ointment.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
|---|---|
| Active compound (as free compound or salt thereof) | 100 mg |
| Colloidal silicon dioxide (AEROSIL) | 1.5 mg |
| Cellulose, microcryst. (AVICEL) | 70 mg |
| Modified cellulose gum (AC-DI-SOL) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

Any novel feature or combination of features described herein is considered essential to this invention.

PHARMACOLOGICAL EFFECTS

Male Sprague Dawley rats ( 300±25 g) were anesthetized with pentobarbital sodium (50 mg/kg i.p.) and polyethylene catheters were positioned in both femoral veins for the intravenous administration of drugs, such as nociceptin and analogues, and into the left femoral artery in order to measure arterial blood pressure and heart rate.

The trachea was cannulated with polyethylene tubing and the rat was pithed, ventilated and drug treated as described by Nuki Y. et al. (Effects of Dorsal Rhizotomy on Depressor Response to Spinal Cord Stimulation Mediated by Endogenous Calcitonin Gene-related Peptide in the Pithed Rat. J. Neurosurg. 1993; 79: 899–904).

EXAMPLES

Prior administration of nociceptin and related analogs inhibited the depressor response to spinal cord stimulation accordingly:

| Structure | dose (mg/kg) | mean reduction (% of maximal depressor response) |
|---|---|---|
| nociceptin | 0.1 | 29 ± 9 |
|  | 0.3 | 23 ± 6 |
| Ac—Arg—Tyr—Tyr—Arg—Trp—Lys—NH$_2$ | 0.1 | 54 ± 12 |
|  | 0.3 | 32 ± 7 |

A clear dose-response was observed for the hexapeptide, Ac-Arg-Tyr-Tyr-Arg-Trp-Lys-NH$_2$. In all animals examined, the effect of both nociceptin and the hexapeptide was seen when repeated a second time after a second non-antagonized depressor response.

What is claimed is:

1. A method for treating migraine, Type II diabetes, sepsis, inflammation and/or vasomotor disturbances, the method comprising administering to a patient in need thereof an effective amount of a compound of formula (I)

$$A^1\text{-}A^2\text{-}A^3\text{-}A^4\text{-}A^5\text{-}A^6\text{-}Y \qquad (I)$$

wherein $A^1$ is Arg, Lys, His, D-Arg, D-Lys, D-His, acylated Arg, acylated Lys, acylated His, acylated D-Arg, acylated D-Lys or acylated D-His;

$A^2$ is Tyr, Trp, Phe, D-Tyr, D-Trp or D-Phe;

$A^3$ is Tyr, Trp, Phe, D-Tyr, D-Trp or D-Phe;

$A^4$ is Lys, Arg, His, D-Arg, D-Lys or D-His;

$A^5$ is Phe, Tyr, Trp, Ile, D-Phe, D-Tyr, D-Trp or D-Ile;

$A^6$ is Arg, Lys, His, D-Arg, D-Lys or D-His; and

Y is OH or NH$_2$ or a pharmaceutically acceptable salt thereof.

2. The method of claim 1 wherein said amino acids are in the L stereochemical configuration.

3. The method of claim 1 wherein $A^1$ comprises acetylated Arg.

4. The method of claim 1 wherein $A^2$ comprises Tyr.

5. The method of claim 1 wherein $A^3$ comprises Tyr.

6. The method of claim 1 wherein $A^4$ comprises Arg or Lys.

7. The method of claim 1 wherein $A^5$ comprises Trp or Ile.

8. The method of claim 1 wherein $A^6$ comprises Arg or Lys.

9. The method of claim 1 wherein Y is NH$_2$.

10. The method of claim 1 wherein said amino acids are all in the D stereochemical configuration.

11. The method of claim 1 wherein the compound is selected from the group consisting of Ac-Arg-Tyr-Tyr-Arg-Trp-Arg-NH$_2$, Ac-Arg-Tyr-Tyr-Arg-Trp-Lys-NH$_2$, Ac-Arg-Tyr-Tyr-Arg-Ile-Lys-NH$_2$, Ac-Arg-Tyr-Tyr-Lys-Trp-Arg-NH$_2$ and Ac-Arg-Tyr-Tyr-Lys-Trp-Lys-NH$_2$.

12. The method of claim 1 wherein the compound is administered in a form suitable for oral, nasal, transdermal, pulmonal, or parenteral administration.

13. The method of claim 1 wherein the compound is administered as a dose in the range from about 0.001 g to about 10 g per patient per day.

14. The method of claim 1 wherein the vasomotor disturbances are hot flushes or hot flashes.

* * * * *